United States Patent [19]

Anson et al.

[11] Patent Number: 5,171,569
[45] Date of Patent: Dec. 15, 1992

[54] FACTOR IX PREPARATIONS UNCONTAMINATED BY PLASMA COMPONENTS OR POX VIRUS

[75] Inventors: Donald S. Anson, Hailey; George G. Brownlee; Ian M. Jones, both of Oxford, all of England

[73] Assignee: National Research Development Corporation, London, England

[21] Appl. No.: 764,073

[22] Filed: Sep. 23, 1991

Related U.S. Application Data

[63] Continuation of Ser. No. 403,784, Sep. 6, 1989, abandoned, which is a continuation of Ser. No. 839,215, Mar. 13, 1986, abandoned.

[30] Foreign Application Priority Data

Mar. 15, 1985 [GB] United Kingdom ............... 8506767
Jun. 18, 1985 [GB] United Kingdom ............... 8515416

[51] Int. Cl.$^5$ .................. C07K 13/00; A61K 37/54; A61K 37/48; C12N 9/48
[52] U.S. Cl. .................. 424/94.64; 435/219; 514/8; 530/381; 530/384
[58] Field of Search .................. 435/69.1, 69.6, 172.3, 435/219; 514/2, 8, 12; 530/350, 380, 381, 384, 395, 829; 424/94.64

[56] References Cited

U.S. PATENT DOCUMENTS

| | | | |
|---|---|---|---|
| 3,920,625 | 11/1975 | Andersson et al. | 530/382 |
| 4,348,384 | 9/1982 | Horikoshi et al. | 514/21 |
| 4,379,085 | 4/1983 | Williams et al. | 530/384 |
| 4,405,603 | 9/1983 | Schwinn et al. | 424/101 |
| 4,770,999 | 9/1988 | Kaufmann et al. | 435/68 |
| 4,994,371 | 2/1991 | Davie et al. | 435/172.3 |

FOREIGN PATENT DOCUMENTS

| | | |
|---|---|---|
| 200421A | 12/1086 | European Pat. Off. |
| 107278A | 5/1984 | European Pat. Off. |
| 162782A | 11/1985 | European Pat. Off. |
| 2564106 | 11/1985 | France |
| 8505125 | 11/1985 | PCT Int'l Appl. |
| 2125409 | 3/1984 | United Kingdom |

OTHER PUBLICATIONS

H. Suomela et al., Eur. J. Biochem. 71, 145-154 (1976).
A. Yoshioka et al., Brit. J. Haematology 59, 265-275 (1985).
K. Kurachi and E. W. Davie, Proc. Natl. Acad. Sci. USA 79, 6461-6464 (1982).
K. Katayama et al., Proc. Natl. Acad. Sci. USA, 76, 4990-4994 (1979).
R. A. McGraw et al., Proc. Natl. Acad. Sci. USA, 82, 2847-2851 (1985).
B. B. Knowles et al., Science 209, 497-499 (1980).
"A Laboratory Manual of Blood Coagulation" by D. E. G. Austen and I. L. Rhymes, pp. 59 and 81-89, Blackwell Scientific Publications Ltd., Oxford (1975).

(List continued on next page.)

Primary Examiner—Robert A. Wax
Assistant Examiner—Stephen Walsh
Attorney, Agent, or Firm—Nixon & Vanderhye

[57] ABSTRACT

The blood-clotting protein, factor IX, is synthesized in the bod in liver cells, where it undergoes three distinct types of post-translational modification before it is secreted into the bloodstream as a 415 amino acid long protein. It is therefore a difficult protein to produce by recombinant DNA technology in a highly biologically active form. Nevertheless, such a result has been achieved by the present invention in which typically factor IX cDNA in a plasmid is linearized and inserted into an expression vector having a promoter sequence of SV40 early gene, an SV40 polyadenylation sequence, the TK/NEO selectable marker and an ampicillin resistance gene. Mammalian cells such as from a dog kidney or rat liver are transfected by the calcium phosphate precipitation method. High levels of factor IX in a fully or near-fully biologically active form, useful as a plasma-free preparation for treatment of patients suffering from Christmas Disease (haemophilia B), are obtainable without recourse to poxvirus vectors which would contaminate the protein.

4 Claims, 5 Drawing Sheets

OTHER PUBLICATIONS

A. H. Goodall et al., Blood 59(3), 664–670 (1982).

McMullen et al, "The Occurrence of . . . " Biochem. & Biophy. Research Communications, vol. 115, No. 1, Aug. 30, 1983, pp. 8–14.

Chavin et al, "Blood clotting Factor IX" The Journal of Biological Chemistry, vol. 259, No. 6 Mar. 25, 1984, pp. 3387–3390.

Morita, et al. "Derivatives of Blood Coagulation . . . " The Journal of Biological Chemistry, vol. 259, No. 9, pp. 5698–5704.

Austen et al, "A Laboratory Manual of Blood Coagulation" Blackwell Scientific Publications, p. 59.

D. S. Anson et al., EMBO. J. 3, 1053–1060 (1984).

L. Wasley et al., Blood, Supplement to the Nov. 1985 issue, p. 1256.

H. de la Salle et al., Nature 316, 268–270 (Jul. 18, 1985).

S. Busby et al., Nature 316, 271–273 (Jul. 18, 1985).

D. S. Anson et al., Nature 315, 683–685 (Jun. 20, 1985).

F. Colbére—Garapin et al., J. Mol. Biol. 150, 1–4 (1981).

F. G. Grosveld et al., Nucleic Acids Research 10, 6715–6732 (1982).

R. C. Mulligan et al., Science 209, 1422–1427 (1980).

T. W. Munns et al., Proc. Natl. Acad. Sci. USA, 73 2803–2807 (1976).

Jallat et al, *EMBO Journal* 9: 3295–3301, 1990.

W. I. Wood et al., *Nature* 312: 330–336, Nov. 22, 1984.

G. E. Schulz and R. H. Schirmer, Principles of Protein Structure, 1979, pp. 14–16.

Suomela, Chem. Abs, 86:40873u, 1977, p. 314.

Bloom, Nature, 303, 474–5, (1983).

Fujikawa et al, Biochemistry, 12(29), 4938–45, (1973).

Osterud et al, J. Biol. Chem., 253(17), 5946–51, (1978).

FACTOR IX PREPARATIONS UNCONTAMINATED BY PLASMA COMPONENTS OR POX VIRUS

This is a continuation of application Ser. No. 07/403,784, filed Sep. 6, 1989, now abandoned which is a Rule 62 continuation of U.S. Ser. No. 06/839,215 filed Mar. 13, 1986, now abandoned.

BACKGROUND OF THE INVENTION

1. Field of the Invention

This invention relates to factor IX protein, a protein involved in the blood-clotting mechanism of warm-blooded animals, and its production by recombinant DNA technology.

2. Description of Prior Art

Haemophilia B, or Christmas disease, is an inherited, X-linked bleeding disorder caused by a defect in clotting factor IX. Injection of factor IX concentrate obtained from blood donors allows most patients to be successfully managed. However, due to impurities in the factor IX concentrate in use at present, this treatment involves some risk of infection by blood-borne viruses such as non-A, non-B hepatitis virus and the virus that causes AIDS. Despite recent apparent success in the heat-inactivation of the virus which causes AIDS, non-A non-B hepatitis virus remains resistant, see P. M. Mannucci et al., Lancet (ii) page 1013 (Nov. 2, 1985). Because of the considerable risk of viral infection in haemophiliacs, a factor IX preparation derived from a source other than blood is desirable.

Factor IX DNA was cloned in 1982, see K. H. Choo et al., Nature 299, 178-180 (1982), K. Kurachi et al., Proc. Nat. Acad. Sci. USA 79, 6461-6464 (1982) and European Patent Application Publication No. 107278A (NRDC). The work is summarised with sequence data and genome maps by D. S. Anson et al., EMBO J., 3 1053-1060 (1984) as well as in the above Patent Application.

Factor IX is a plasma glycoprotein which plays an essential role in the middle phase of the intrinsic clotting pathway where, in an activated form, IXa, it interacts with factor VIII(C), phospholipid and calcium ions to form a complex that converts factor X to Xa. Factor IX is synthesised in liver hepatocytes where the 461 amino acid long primary translation product (precursor) undergoes at least two stages of protein processing involving peptide cleavage as well as three distinct types of post-translational modification, before secretion into the bloodstream as a 415 amino acid long mature, biologically active glycoprotein.

The post-translational modifications are the vitamin K-dependent carboxylation of twelve glutamic acid residues, the addition of several carbohydrate residues and the beta-hydroxylation of a single aspartic acid residue. The first two modifications are known to be required for activity. Additionally, "prepeptide" and "propeptide" sequences totalling 46 amino acids have been removed as part of the processing of the precursor to give the mature, active protein. The precursor is not active in the blood-clotting pathway. Because of the complex and specialised nature of the processing and these modifications, it seemed probable that the expression of active factor IX derived from factor IX DNA clones, would present great problems.

The difficulties of obtaining a fully biologically active factor IX protein are amply illustrated by prior art which has been published between the priority dates and filing date of the present application.

L. Wasley et al., Blood, Supplement to the November 1985 issue, page 1256 describe expression of a factor IX gene in Chinese hamster ovary cells. The cells secreted over 100 micrograms/ml of a material having the antigenic characteristics of factor IX but of which only 1.5 micrograms/ml was native factor IX, i.e. was biologically active. The authors commented: "Current efforts are directed at improving the efficiency of gammacarboxylation and increasing the percentage of Factor IX that is biologically active."

Transgene S. A. filed a French Patent Application 8407125 on May 9, 1984 which has been published on Nov. 15, 1985 as U.S. Pat. No. 2,564,106. There are foreign counterparts, also published, including WO85/05125 (Japan, USA) and European Patent Application Publication No. 167420A. These specifications describe cloning of the factor IX gene in *E. coli* and transfecting mammalian cells by theccalcium phosphate precipitation method. Mice embryo fibroblast cells were thus transfected, resulting in expression of proteins of molecular weight 62,000 and 72,000 daltons. Both proteins reacted with anti-factor IX antibodies, the 62,000 dalton protein was shown to be glycosylated, and a preliminary study showed that the antigen had carboxylated glutamic acid groups. The specifications speculated that the proteins thus obtained were factor IX precursors. That of molecular weight 62,000 daltons appears to be the primary translation product, since its extra molecular weight of about 5,000 daltons is readily accounted for by its possessing the additional 46 amino acids referred to above (assuming an average of molecular weight of 112 for an amino acid, $46 \times 112 = 5152$). It is noteworthy that Transgene S.A. did not perform a clotting assay or do any other test to indicate that the protein precursors described were biologically active. In all the circumstances, therefore, the reasonable conclusion is that the Transgene S.A. specifications do not describe mature, fully or even near-fully biologically active factor IX protein.

It is interesting that Transgene S.A. refer to the possibility of transfecting bovine kidney (MDBK) and monkey kidney (VERO) cell lines, see page 49 of the French specification of May 9, 1984 and in this connection say (in translation): "Some results have been obtained from the cells N1H-3T3 and LMTK (the mouse embryo fibroblasts) and are actually in progress for the lines MDBK and VERO". However, in the specifications filed at the end of the convention priority year in May 1985, precisely the same statement (word for word identical) appears. The reasonable conclusion is that there were considerable difficulties associated with the work in progress or that it was not felt worthwhile pursuing further the possibility of using these other cell lines.

Transgene S.A. also filed French patent applications on May 22, 1984 and Oct. 5, 1984, from which European Patent Application Publication No. 162782A published Nov. 27, 1985 claims priority. This specification describes expression of factor IX in vaccinia virus and cowpox virus. See also H. de la Salle et al., Nature 316, 268-270 (Jul. 18, 1985). The procedure involves infecting cells in which the poxvirus grows but which were ultimately killed by the virus. This gives high yields while the virus is growing, but which rapidly decrease to zero (usually within 24 hours). Control of the process presents serious problems for this reason and because there are two "biological reactants" requiring careful quality control, the cells and the virus stock. Substantial amounts of product failed to adsorb to barium sulphate, indicating that it had only about 50% of the biological activity of normal plasma factor IX. An even more serious problem is that the factor IX protein thus produced would have to be purified rigorously to remove live poxviral particles and antigens from the dead poxvirus, before the factor IX protein could be given to human patients. Vaccinia virus is a Class 2 human pathogen and can kill people who are seriously immunosuppressed.

Production of 50–60% biologically active human factor IX by transfection of Baby Hamster Kidney cells with factor IX cDNA has been reported by S. Busby et al., Nature 316, 271–273 (Jul. 18, 1985).

The subject matter of the present invention was published by D. S. Anson et al., Nature 315, 683–685 (Jun. 20, 1985).

SUMMARY OF THE INVENTION

It has now been found possible to produce an artificial fully or near-fully biologically active factor IX protein by a recombinant DNA process in mammalian cells without recourse to poxvirus vectors.

The full or near-full biological activity of the factor IX protein of the invention can be defined in various ways. A preferred definition relates to the antigenic activity of the molecule to its clotting activity (both relative to the factor IX of normal blood plasma). Thus, in one aspect the present invention provides biologically active recombinant DNA-derived factor IX protein having a specific activity defined as $$\frac{\text{Clotting activity}}{\text{Antigenic concentration as determined by ELISA}}$$

of at least 90% of that of blood-derived factor IX, and free from contamination by poxvirus proteins. Alternatively or additionally the factor IX protein can be defined as having a molecular weight of about 57 kilodaltons and free from contamination by precursor factor IX to an extent of more than 10 weight % and by poxvirus proteins.

Preferably the factor IX protein of the invention is human factor IX protein or sufficiently similar thereto to be acceptable for infusion into human patients suffering from factor IX deficiency.

According to an important aspect of the invention artificial factor IX protein is prepared by a process which comprises preparing a recombinant expression vector by linking a factor IX DNA sequence to a promoter sequence effective to express the DNA in a eukaryotic cell incorporating these DNA sequences in a vector, and introducing this expression vector into eukaryotic, preferably mammalian, cells in vitro, the eukaryotic cells having or being provided with post-translational modifying means effective to modify the biologically inactive product of the expression of the DNA into biologically active factor IX protein.

Preferred such cells are kidney and liver cells of mammals, including humans.

The invention further includes specifically mammalian cells, as defined above, especially from the preferred commercially available dog kidney cell line, transfected with a bacterial host, especially a transformation-competent E. coli, containing a plasmid pIJ5/9 or the like as defined above.

DESCRIPTION OF THE PREFERRED EMBODIMENTS

Figure 1:
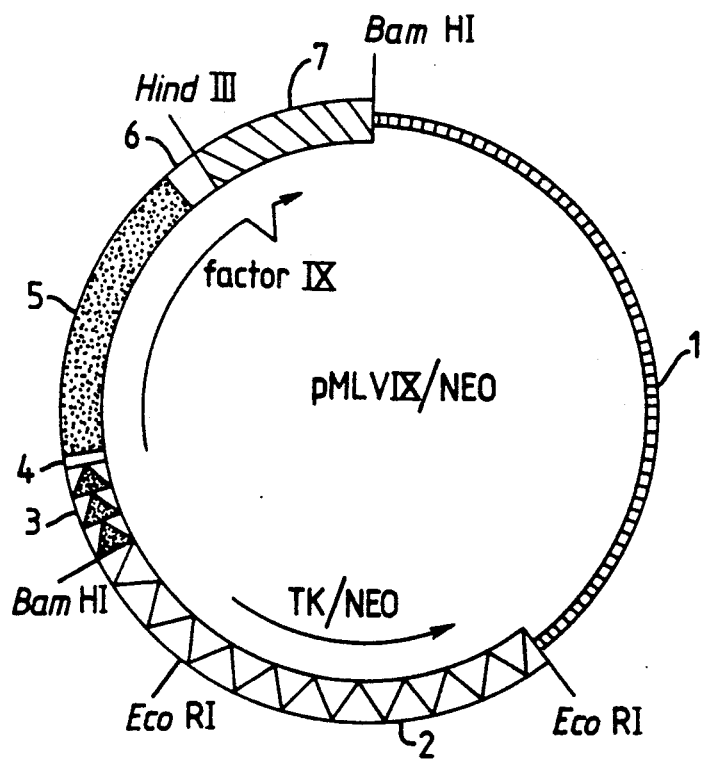
FIG. 1 shows schematically a recombinant expression vector which can be used to transfect mammalian cells and which contains human factor IX DNA.

The invention is applicable primarily to human factor IX, although it could in principle be applied to animal factor IX. For example, bovine factor IX complementary DNA cloned sequences are described in the NRDC European Patent Application supra and they could be used to isolate full-length bovine complementary DNA clones, which could be expressed in a similar manner to that described here for human factor IX genes.

The term "factor IX DNA" is used herein to mean a DNA complementary to factor IX mRNA or derived from the exon regions of the factor IX gene by artificially removing intron sequences, which would yield upon translation in vivo a primary protein which can be modified by carboxylation of its glutamic acid residues, addition of carbohydrate residues and, if necessary, hydroxylation of an aspartic acid residue as mentioned above, to give a biologically active factor IX protein.

The factor IX DNA employed can be any likely to yield factor IX after modification and will therefore normally include the cDNA complementary to that part of the mRNA which codes for the primary translation product. This includes the sequence coding for amino acids minus 1 to minus 46 designated as "PRE" and "PRO" by Anson et al., supra, FIG. 6 on page 1058. "PRE" amino acids form a hydrophobic signal region (−46 to −21), "PRO" a hydrophilic precursor region (−20 to −1). "PRE" or "PRO"-coding mRNA sections could be replaced by foreign sequences.

Conveniently therefore the DNA includes a sequence which codes for the precursor region of the primary translation product lying to the 5'-end of that part of the mRNA which gives rise to the mature (biologically active) protein. It will also be appreciated that the DNA can contain point mutations not affecting the amino acids coded for, as well as mutations, deletions and additions of nucleotides or short sequences thereof which alter the amino acids but do not materially affect the mature protein. Up to 5% or even up to 10% of the DNA might be expected to be so varied.

For expression a eukaryotic cell or viral promoter is required. The Moloney Leukemia Virus LTR promoter and the SV40 early gene promoter have both been used successfully. The chosen promoter is linked to the 5'-end of the factor IX DNA. Ordinarily each will be present initially in its own vector. One of the vectors is restricted to excise the DNA and the other restricted to accommodate transfer thereto of the excised fragment, and the two are ligated. It would be expected that other viral promoters, such as the thymidine kinase gene promoter of Herpes simplex virus or the major late promoter of Adenovirus would be satisfactory. Equally the factor IX promoter could be used but might be less active than the viral promoters. An AAUAAA polyadenylation signal, N. J. Proudfoot and G. G. Brownlee, Nature 263, 211-214 (1976), is provided by the SV40 early gene polyadenlyation region of sequence, but others including the natural factor IX signal would be expected to function satisfactorily.

The vectors referred to herein are conveniently cloned into E. coli in manner known per se for bulking up.

The expression vector preferably also includes a selectable marker to enable selection of mammalian cells into which the factor IX gene has been introduced. The marker may comprise a prokaryotic DNA transposon sequence linked to a eukaryotic DNA promoter sequence, as for example in the TK/NEO gene.

In principle the kind of mammalian cell line most likely to be useful in the invention would be a hepatic cell or a transformed cell line derived from a hepatocyte. Unfortunately, none of the standard mammalian cell lines is known to secrete active endogenous factor IX. However, the rat hepatoma cell line H4-11-E-C3 (ATCC 1600) is known to secrete prothrombin which is gamma-carboxylated, indicating the presence of a gamma-carboxylase enzyme which might also serve to carboxylate the intermediate protein in the production of factor IX. This cell line has proved successful, but a commercially available dog kidney cell line not known to have any such modification "machinery" has proved to be even more successful. The cells must inherently possess or be provided with the necessary means of modifying the primary translation product or inactive protein to produce a protein which exhibits substantial factor IX activity. Cells likely to have the gamma-carboxylase enzyme are liver and kidney cells. Those which lack it can be supplied with it by cloning the gene for this enzyme (by constructing a rat liver cell library, amino acid sequencing of parts of the purified carboxylase enzyme, constructing oligonucleotide probes, probing the library and testing the clones for carboxylase activity and then transfecting the gamma-carboxylase deficient cells with the cloned gene.

The introduction of the factor IX gene into mammalian cells may be carried out by the calcium phosphate precipitation technique. In this method a solution of the DNA to be transfected is made up in disodium phosphate. On the addition of calcium chloride, a fine precipitate of calcium phosphate is obtained in which DNA is trapped. After overlaying cells with this precipitate, some cells take up crystals of calcium phosphate along with the entrapped DNA. Within the cell the calcium phosphate crystals dissolve leaving the DNA free in some cases to integrate into the genome. Other known means of introducing DNA into cells are usable, such as protoplast fusion, W. Schaffner, Proc. Nat. Acad. Sci.USA 77, 2163-2167 (1980); electroporation, H. Potter et al., Proc. Nat. Acad. Sci. USA 81, 7161-7165 (1984) and infection with retroviruses, e.g. A. D. Miller et al., Proc. Nat. Acad. Sci. USA 80, 4709-4713 (1983).

The factor IX protein can readily be recovered from the medium in which the transfected cells are grown, without the need for lysis. The protein is preferably purified by affinity chromatography. For this purpose an antibody, preferably a monoclonal antibody to factor IX, most preferably one which is anti- to a metal ion-dependent epitope of factor IX antigen, is attached by conventional means to a support material on a column and the factor IX - containing product is adsorbed onto the column. To elute it, an appropriate metal chelating agent, in the case exemplified by Example 3, or a chaotrope, in the case exemplified by Examples 1 and 2, or a disrupting agent can be employed, and it has been found that a mixture of a high molar concentration of urea, say about 6-8M, with an inorganic salt, for example about 0.8 to 1.2M of an alkali metal chloride, in admixture therewith is particularly useful for this purpose.

The following Examples illustrate the invention.

EXAMPLE 1

The general scheme of the preparation and analysis of factor IX protein is as follows:

1. Construction of a factor IX DNA sequence. A full length sequence of factor IX cDNA (complementary to factor IX mRNA) was prepared.
2. Construction of an expression vector designed to express factor IX protein in eukaryotic cells. This vector herein termed pMLV/NEO, was constructed from the following component elements.
   (a) a promoter for expression of the long terminal repeat (LTR) of the Moloney Leukemia Virus (MLV);
   (b) the small t antigen intron of Simian Virus 40 vector (SV40);
   (c) the early polyadenylation signal sequence from SV40; and
   (d) the TK/NEO gene which provides a marker, by which those eukaryotic cells containing the desired foreign gene can be selected.
3. Insertion of the factor IX DNA sequence into the expression vector pMLV/NEO to give recombinant DNA plasmid pMLV IX/NEO.
4. Transfection of a mammalian cell line with the recombinant DNA plasmid pMLVIX/NEO, whereby the foreign DNA becomes integrated into the chromosomal DNA of the cells.
5. Confirmation of the secretion of fully biologically active factor IX by a one-stage clotting assay and by inhibition of the clotting activity by the addition of a monoclonal antibody to factor IX.
6. In Example 3 comparative studies of protein mobility by gel electrophoresis indicated that the recombinant DNA-derived factor IX Protein of the invention was free from contamination by precursor factor IX in a proportion of more than 10% by weight. The clotting data and other results indicate that the same is true of the factor IX protein produced in Examples 1 and 2.

The preparation and analysis of the factor IX protein will now be described in more detail:

1. Construction of a factor IX DNA sequence

For a detailed understanding of this stage readers are recommended to refer to D. S. Anson et al., EMBO J. 3, 1053-1060 (1984). This paper contains extensive nucleotide sequence information on human factor IX DNA obtained from both factor IX mRNA ("cDNA") and from the human genome ("genomic DNA"). The genome is about 34 kilobases (Kb) long, which is more than 12 times the length of the mRNA, because the genome contains long intron sequences which do not code for the RNA, interspersed with short exon sequences which do. The genomic organisation is shown in the Anson et al. paper.

The mRNA is 2802 residues long and contains a short, 29 nucleotide long 5'- non-coding sequence and an extensive, 1390 nucleotide long 3'-non-coding sequence.

The starting factor IX DNA is the cDNA clone cVI described in FIG. 1 of the Anson et al. paper, containing DNA corresponding to mRNA nucleotides 25 to 1572, but with the first 15 nucleotides inverted and complementary so that they are read 3'→5' instead of 5'→3'. The factor IX DNA insert present in cVI was removed by restriction with BamHI and HindIII and isolated by agarose gel electrophoresis. was necessary to add nucleotides 1-24, and substitute nucleotides of the correct strand for the inverted ones.

The region from nucleotides 25 to 93 was removed from the factor IX cDNA cVI by digesting cVI (held in the plasmid vector pAT153/PvuII/8) with BamHI followed by "filling in" the overhanging ends with deoxynucleoside triphosphates using the Klenow fragment of DNA polymerase I (*E. coli*). After dephosphorylation with calf intestinal phosphatase, a partial digest with EcoRV was performed. EcoRV recognises the sequence GATATC at nucleotides 91-96. A partial digest was necessary because of the presence of an additional EcoRV site at nucleotide 508. The resulting linear fragment of about 4.9 Kb was purified by agarose gel electrophoresis.

A short (0.1 Kb) TaqI/EcoRV fragment was generated from the factor IX genomic DNA XI by digesting XI (also held in the plasmid vector pAT153/PvuII/8) with TaqI, "filling in" the overhanging ends with deoxynucleoside triphosphates as before, in the presence of tracer amounts of alpha-$^{32}$P dGTP and recutting with EcoRV. This labelled fragment, corresponding to nucleotides 288-386 of the genomic DNA, see FIG. 4 of the Anson et al. paper, was separated from other TaqI and EcoRV fragments derived from the plasmid vector by 6% acrylamide gel electrophoresis.

The 4.9 Kb and 0.1 Kb long fragments were ligated together with T4 DNA ligase, the resultant recombinant cloned in *E. coli* was isolated and characterised by standard methods and designated p5'G/3'cVI. This reconstructed factor IX gene therefore contained the sequence corresponding to nucleotides 1-1572 of the mRNA effectively adding nucleotides 1-24 to and correcting the rearrangement in the first 15 residues of clone cVI. It also contained 8 extra nucleotides, genomic DNA residues 288-295, derived from the presumed factor IX promoter region, but these residues alone are not sufficient to specify promotion.

2. Construction of expression vector pMLV/NEO

Figure 5:
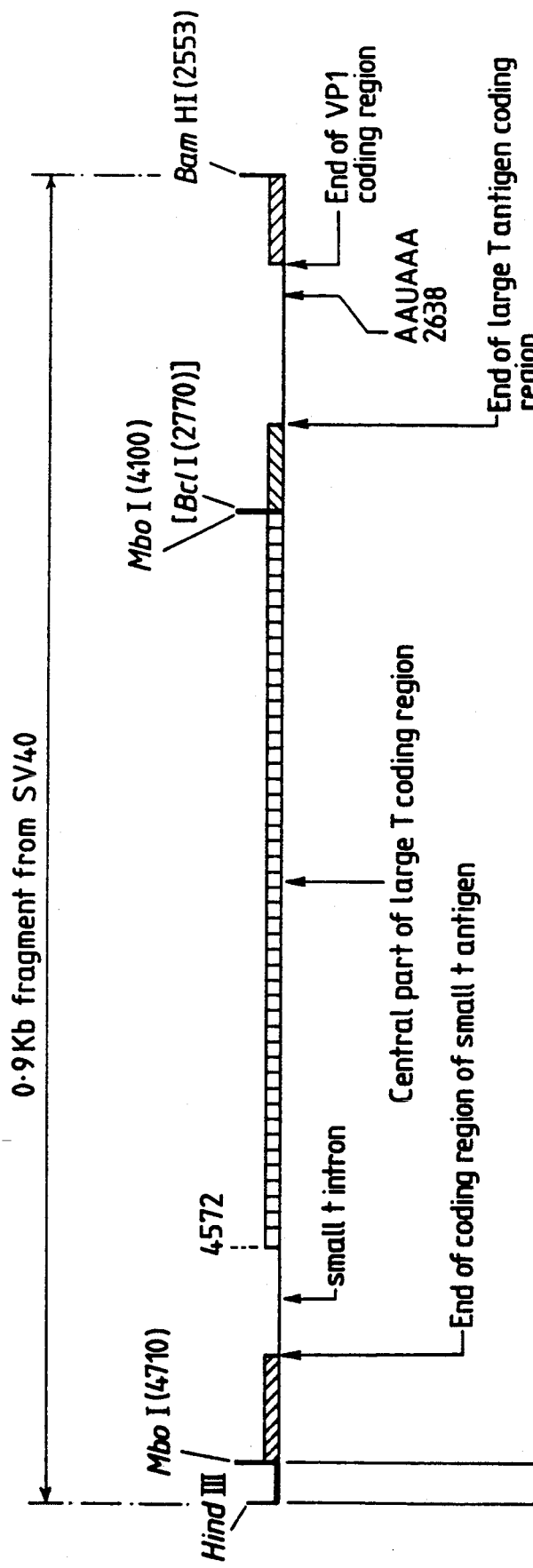
FIG. 5 is a line diagram of a DNA fragment used in constructing the vector of FIG. 1.

The construction started from the plasmid pTKMo1 TK1. This is a pAT153 plasmid containing the thymidine kinase (TK) gene as a marker and the Moloney Murine Leukemia Virus (MLV) Long Terminal Repeat (LTR) sequences. The plasmid was restricted with HindIII and BamHI to remove the TK coding section of sequence. The remainder of the molecule (pAT153 and MLV LTR) was purified by agarose gel electrophoresis. It was then used as a vector for cloning of an agarose gel-purified 0.9 Kb BamHI/HindIII fragment containing the SV40 small t intron and early gene polyadenylation signal which was derived from pSV1 (a gift from Dr Davey, Warwick). FIG. 5 shows a line diagram of this approximately 0.9 Kb fragment which is composed of 3 parts. The first is a synthetic deoxyoligonucleotide sequence of 21 residues providing a TGA chain termination stop codon in each of the 3 possible reading frames. The second derives from the MboI 610 long fragment from residues 4710-4100 of SV40 virus (see pp 799-841 in "DNA tumour viruses, Molecular Biology of Tumour Viruses", second edition, Part 2 (revised) Ed. J. Tooze, Cold Spring Harbor Laboratory, 1981). This fragment provides the small t antigen intron bounded by parts of the small t and large T antigen coding regions. The third part derives from the BclI site, originally at nucleotide 2770, but eliminated in the re-construction shown in site (residue 2553) of SV40 virus and contains the AAUAAA SV40 polyadenylation sequence at residue 2638 as well as parts of the large T antigen and VP1 coding region. The small t antigen intron was included in this expression vector in case this was required for expression of protein. However, the absence of this element in the second expression vector (see Example 2, below) showed that it was unnecessary. Recombinants containing the 0.9 Kb fragment were identified by restriction mapping and one was chosen and designated pMLV. pMLV was restricted with PvuI and EcoRI, and the EcoRI ends blunt-ended by "filling in" using the Klenow fragment of DNA polymerase I. The 4.4 Kb PvuI/EcoRI fragment containing the MLV LTR, SV40 sequences and most of the pAT153 sequences was purified by agarose gel electrophoresis.

A thymidine kinase/neomycin-kanamycin (TK/NEO) gene was then prepared. Such a gene is described by F. Colbére—Garapin et al., J. Mol. Biol. 150, 1-4 (1981). It was constructed by linking the eukaryotic promoter region (EPR) for the transcription of the TK gene in Herpes Simplex Virus type I to the well known transposon Tn5 which codes for the enzyme aminoglycoside-3'-phosphotransferase type II (APH(-3')-II) conferring kanamycin resistance. When mammalian cell lines were transfected with this TK/NEO gene they exhibited resistance to the aminoglycoside G418, an antibiotic, thus indicating that the APH(3')-II gene had become incorporated and the APH(3')-II enzyme expressed in the eukaryotic DNA of the mammalian cells. The TK/NEO gene is thus a valuable dominant selective marker in eukaryotic cells.

The TK/NEO gene and part of the amp-r gene was purified as a PvuI/BamHI fragment from the cosmid vector pTM, F. G. Grosveld et al., Nucleic Acids Research 10, 6715-6732 (1982). The BamHI end was made blunt-ended by "filling in" (see above). This fragment was then ligated to the pMLV-derived PvuI/EcoRI fragment using T4 DNA ligase and recombinants selected on ampicillin. Note that the PvuI site interrupts the amp-r gene so that in this ligation the amp-r gene was reconstructed in part from one fragment and in part from the other. The structure of recombinants was checked by restriction mapping and one clone, designated pMLV/NEO, was used in the next stage.

3. Insertion of factor IX DNA sequence into plasmid pMLV/NEO to form recombinant plasmid pMLVIX/NEO The isolated factor IX DNA from Stage 1 was then ligated into the HindIII site of the expression vector pMLV/NEO from Stage 2 by the use of T4 DNA ligase and the Klenow fragment of DNA polymerase I.

Clones containing the factor IX DNA insert in the correct orientation were identified by restriction mapping, and one such clone, pMLVIX/NEO, was used in the next stage. FIG. 1 of the drawings shows pMLVIX/NEO. The factor IX and TK/NEO transcription units are indicated by arrows which indicate the 5'→3' direction of the mRNA transcribed from these genes. (Note for lay readers: since the cDNA in the plasmid is double-stranded, it is meaningless to specify a direction of the DNA itself. Only one of the two strands would be transcribed into RNA and the arrow indicates the 3'→5' direction of the strand which is transcribed). pAT153 sequences are shown by the narrow filled line (1), the TK/NEO gene by the zig-zag line (2). The factor IX transcription unit, from 5' to 3', consists of the MLV LTR (solid triangles, 3) factor IX 5' non-coding sequence (open wide line, 4), factor IX coding sequence (filled wide line 5) part of the factor IX 3' non-coding sequence (open wide lines, 6) and SV40 sequences (diagonals, 7). The total length of the DNA is about 9.0 Kb.

4. Transfection of a mammalian cell line with the recombinant plasmid pMLVIX/NEO carrying a human factor IX gene The rat hepatoma line, H4-11-E-C3 deposited at the American Type Culture Collection as an open deposit ATCC 1600, was transfected with the factor IX expression plasmid by calcium phosphate precipitation, as follows. The DNA of interest was made up in HBS buffer to a concentration between 10-50 micrograms ml-1 The HBS buffer contains 137 mM NaCl, 5 mM KCl, 0.7 mM $Na_2PO_4$, 5 mM glucose, and 20 mM Hepes pH 7.05. $CaCl_2$ was added from a concentrated (2.5M) stock to a final concentration of 0.125M. The mixture was left at room temperature for 30 minutes during which a fine precipitate formed. The precipitate was layered onto the washed monolayer of tissue culture cells and left at 37° C. for 30 minutes. The monolayer was then overlayed with complete growth medium and incubation was continued overnight at 37° C. The following morning the medium and precipitate were removed and replaced with a solution of 15% glycerol. After incubation at room temperature for 2-3 minutes the glycerol was removed and replaced with fresh medium. Cells containing a functional TK/NEO gene were selected for G418 resistance by the addition of G418 at 400 micrograms/ml 48 hours after the transfection and glycerol shock treatment and 24 of the resultant colonies were amplified by growing in 0.7 cm diameter wells of a 96-well multititre dish. Cells were removed from such wells by standard trypsin treatment, counted in a haemocytometer, diluted to about 3 cells/ml of medium and then 0.2 ml was dispensed into each well of a new 96-well dish. Colonies grew in about 10 weeks and one of each set was chosen as the permanent cell line. It was then grown up and the growth medium assayed for the presence of secreted human factor IX using an enzyme-linked immunosorbent assay (ELISA) as described in Stage 5 below. Four of the cell lines secreted detectable levels of factor IX. The highest producer, line 4A, was chosen for further analysis. Southern blot analysis indicated that there was only 1 copy of the plasmid integrated into chromosomal DNA per cell. Northern blot analysis of total cellular RNA derived from line 4A revealed the presence of a factor IX mRNA species of about 1.6 Kb, which is the expected size of the factor IX transcription unit. In both the Southern and Northern blot analysis no cross-hybridising species was detectable in the control hepatoma cell line H4-II-E-C3.

5. Confirmation of the secretion of human factor IX

Cells were seeded at 10% confluency in a monolayer in an 80 $cm^2$ flask containing 10 ml of medium (MEM, 10% FCS containing penicillin, streptomycin, kanamycin and 100 ng/ml vitamin K). The medium was changed every 24 hours and the conditioned medium assayed by an ELISA for human factor IX. The ELISA was done by first binding 0.2 ml of a mouse anti-factor IX monoclonal antibody 3A6, diluted 1 in 5000 in 200 mM sodium carbonate pH 9.0 to microtitre wells at room temperature for two hours. 150 microlitre samples of conditioned medium were then bound overnight at 4° C. The second antibody, 150 microlitres of rabbit anti-human factor IX (Calbiochem-Behring), diluted 1 in 500 in PBS, 1% NP40, 10% horse serum, was then bound at room temperature for two hours. The third antibody, peroxidase-conjugated swine anti-rabbit IgG (Dako), was bound in the same manner. The assay was finally developed with 0.2 ml of 40 mM ABTS (azinodi-(3-ethylbenzthiazole-sulphonic acid)-diammonium salt) in 0.008% $H_2O_2$ in 50 mM citrate buffer pH 4.0 for 30 to 45 minutes. Colour change of the solution was then measured at 405 nm in a spectrophotometer. A standard curve was constructed using 2-fold dilutions of normal plasma in the range of $10^{-3}$ to $10^{-5}$ dilution assuming a concentration of 5 micrograms/ml for plasma factor IX.

The secreted factor IX was tested for its adsorption onto barium sulphate by the procedure of K. Fujikawa et al., "Methods in Enzymology", Volume 45, Academic Press 1976, page 77. This procedure depends on the gamma-carboxylation of the factor IX precursor and the positive values accordingly indicated gammacarboxylation.

Figure 2:
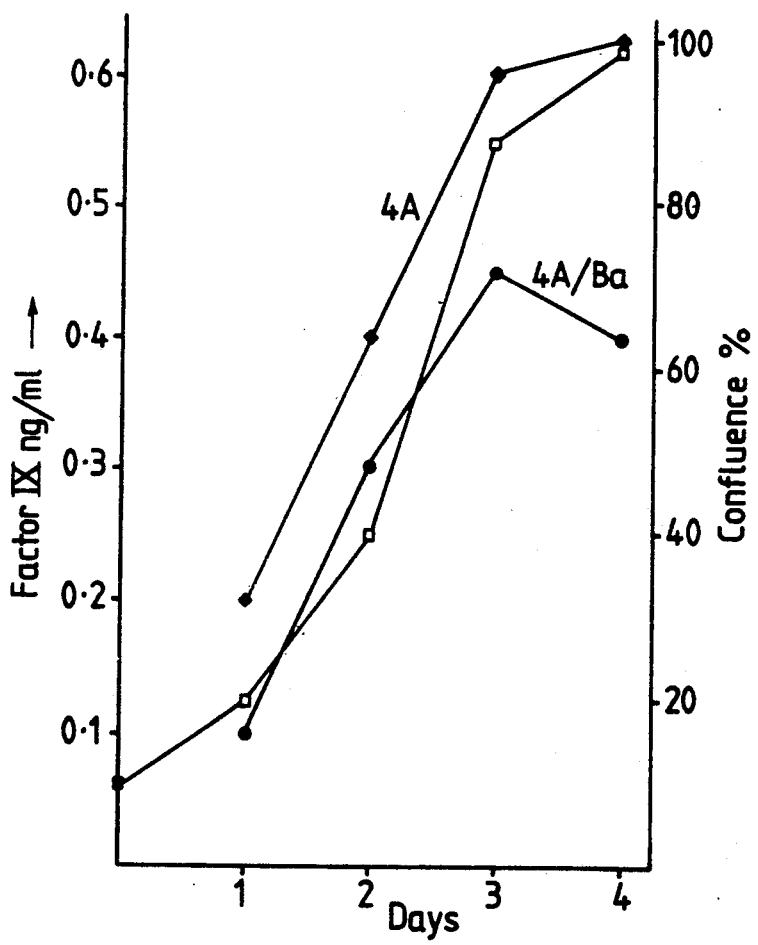
FIG. 2 is a graph showing factor IX levels expressed from a monolayer of confluent mammalian cells transfected with the expression vector of FIG. 1.

FIG. 2 of the drawings shows the time course of the secretion of human factor IX by cell line 4A together with the results of the barium sulphate adsorption test. The solid squares indicate factor IX levels, the solid circles the levels of $BaSO_4$—adsorbed factor IX and the open squares the degree of confluency of the cells. The rate of secretion of factor IX was about 6 ng/$10^7$ cells/24 hours. As the recovery of factor IX is not corrected for possible losses in the procedure, it is not clear from this experiment alone whether about 70% of the factor IX has gamma-carboxyglutamic acid residues, or alternatively, that the material is all gamma-carboxylated and there are losses of about 30% in recovery. The fact that activity correlates well with antigen level (see below) indicates that the latter is the correct explanation. No factor IX was detectable in lysates of the 4A cells, indicating that there was insignificant accumulation inside the cell. No cross-reacting material was detected either in control H4-11-E-C3-conditioned media or in cell lysates.

Clotting and antigenic analyses of a sample of affinity-purified human factor IX from conditioned medium of line 4A cells as well as from a parallel control sample of H4-11-E-C3 cells were performed.

The human factor IX sample from 1.5 litres of conditioned media from line 4A cells, and the control sample from the same volume of H4-11-E-C3 cells were purified by barium citrate adsorption and immunoaffinity chromatography. An anti-human factor IX antibody affinity column was prepared by binding the 3A6 monoclonal antibody, purified from ascites fluid by sodium sulphate precipitation, to the support Affigel 10 (Biorad) using conditions recommended by the manufacturer. Thus the human factor IX sample to be bound was passed twice over the column (column volume =0.3 ml) and it was then washed with over 100 volumes of PBS, 1% NP40 and a similar volume of PBS, 1M NaCl, 1% NP40. Finally the column was then rinsed with 5 volumes of PBS, 1M NaCl and eluted with a 7M urea, 1 M NaCl eluant collecting 0.4 ml fractions. The first three fractions were pooled and immediately dialysed overnight against 2% PBS at 4° C. followed by freeze-drying. The samples were finally dissolved in 200 microlitres water. They were then assayed by ELISA as previously described and subjected to the clotting assay.

Factor IX clotting activity was measured, using the one stage clotting assay in which factor IX deficient plasma is used as a substrate see D. E. G. Austen et al., "A Laboratory Manual of Blood Coagulation", Blackwell Scientific Publications (1975). Human factor IX antigen was measured by ELISA. Both are given as percentages of average normal plasma levels. The inhibition effect of the anti-human factor IX monoclonal antibody 3A6 was measured by preincubation of the sample to be tested with a final concentration of 2.5% 3A6 ascites fluid for 15 minutes at room temperature.

Bovine factor IX antigen was measured in arbitrary units and was assayed by a quantitative ELISA as follows. Dilutions of pure bovine factor IX were diluted in 200 mM sodium bicarbonate pH 9.0 buffer and dried onto microtitre plates. Bovine factor IX was then detected with a polyclonal rabbit anti-bovine factor IX antibody and a peroxidase conjugated swine anti-rabbit IgG antibody, as for the ELISA for human factor IX previously described.

Results of these analyses are shown in Table 1 below:

TABLE 1

Analysis of clotting factor IX activity and human and bovine factor IX antigen in purified sample from cell line 4A

| Assay | Cell Line 4A | H4-11-E-C3 |
|---|---|---|
| Clotting (%) | 7 | 1 |
| Clotting of sample + 3A6 monoclonal antibody (%) | <1 | <1 |
| Human factor IX antigen (%) | 6.8 | not determined |
| Bovine factor IX antigen | 0.8 | 1.2 |

$$\text{Specific activity} = \frac{\text{Clotting activity}}{\text{Antigen concentration}} = \frac{7}{6.8} = 100\%$$

The purified human factor IX protein of the invention from 4A cells was found to be active in a one stage clotting assay, giving an activity level of 7% of normal plasma. Only 1% activity was found in the control from H4-11-E-C3 cells, and this was presumably caused by the trace amounts of bovine factor IX which were found in both line 4A and control samples. An ELISA was therefore performed for bovine factor IX antigen and this indicated the presence of trace amounts in both line 4A and control cells. Further evidence that the cell line 4A is secreting biologically active human factor IX protein was provided by determining the inhibitory effect on the human factor IX of the specific antihuman factor IX monoclonal antibody 3A6 in the clotting assay. Control experiments showed that this antibody does not significantly inhibit bovine or rat factor IX activity at the concentration used.

The fact that the activity level, 7% (of normal plasma), in the line 4A sample correlates well with the human factor IX antigen level, 6.8% (of normal plasma), suggests that the protein is fully active. It was concluded from these results that line 4A cells secrete fully biologically active human factor IX.

EXAMPLE 2

In this Example a different mammalian cell line, one from a dog kidney, and a different promoter were used. A vast increase over Example 1 in the amount of factor IX produced was achieved.

Figure 3:
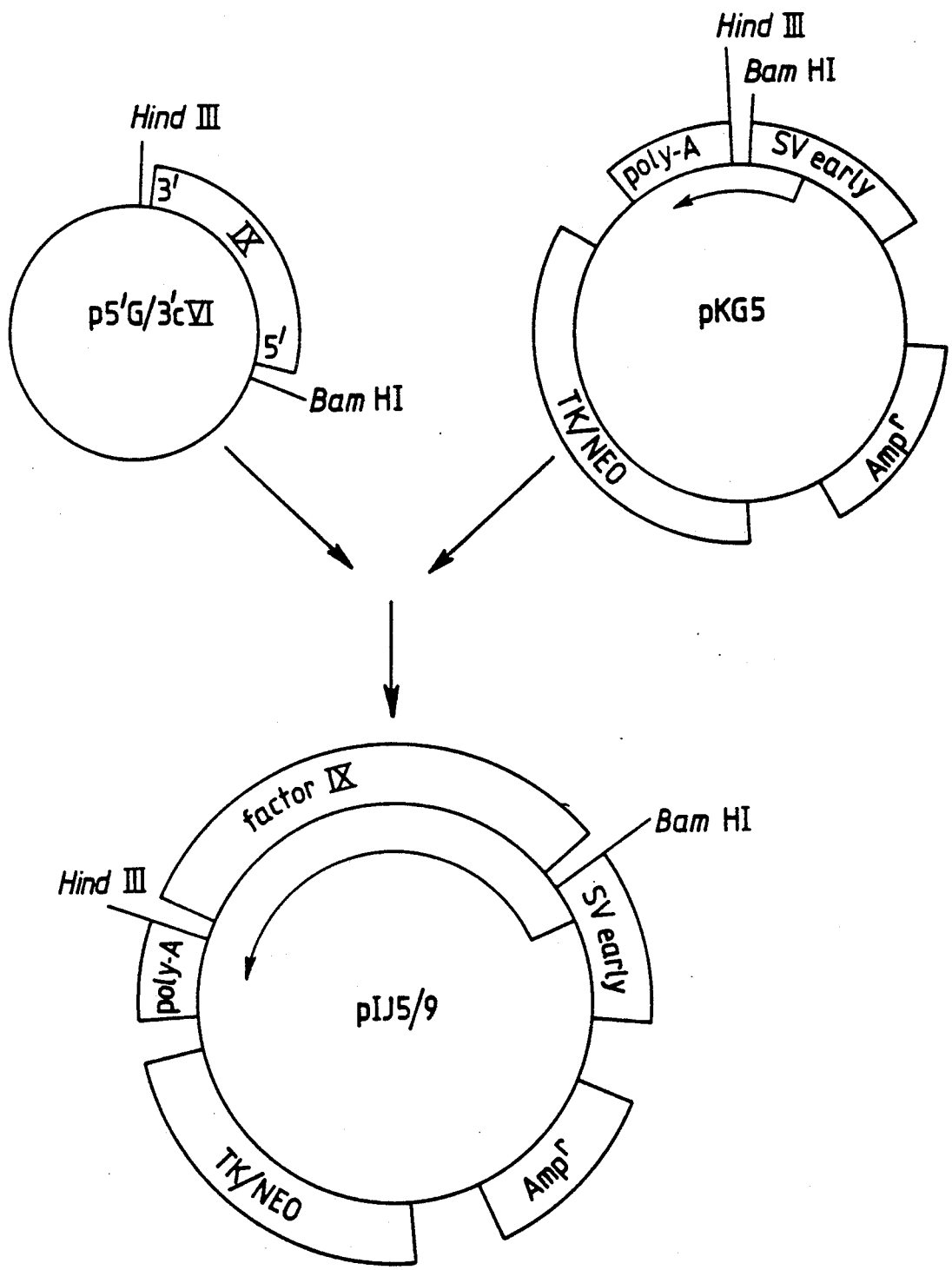
FIG. 3 shows schematically the formation of another recombinant expression vector which can be used to transfect mammalian cells and which contains human factor IX DNA.

FIG. 3 of the drawings illustrates schematically the preparation of recombinant DNA containing the factor IX gene, as described in stages 1-3 below. As in FIG. 1, arrows indicate the direction of transcription of the RNA.

1. Construction of a factor IX DNA sequence
This is as described in Example 1.
2. Construction of expression vector pKG5 pKG5 is a derivative of pSVTKneo, a plasmid expression vector which combines the SV40 early gene promoter and terminator derived from pSV2, see R. C. Mulligan et al., Science 209, 1422-1427 (1980), with the TK/NEO gene derived from the vector pTM, see Example 1.

Figure 6:
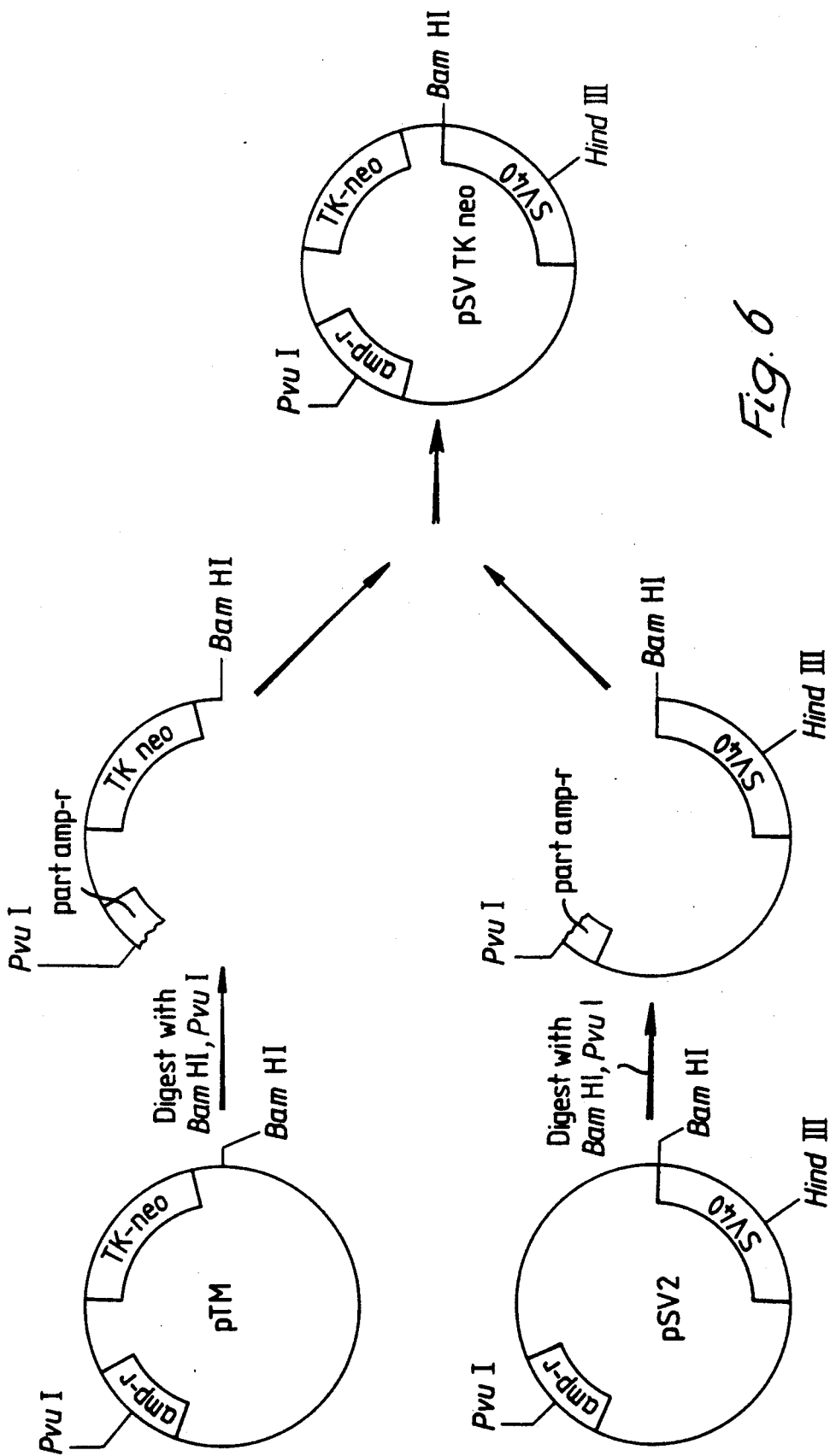
FIG. 6 shows schematically the method of construction of a vector pSVTKneo used as a starting material in the construction of an expression vector for use in the invention.

The construction of pSVTKneo is illustrated in FIG. 6. The plasmid pSV2 was digested with BamHI and PvuI, whereby two fragments were obtained. The smaller was discarded. The larger fragment (which contains a HindIII site) contained part of the ampicillin resistance gene, which was cleaved at the PvuI site, and the whole of the SV40 early gene promoter and polyadenylation sequence. The BamHI cleavage cut pSV2 at the end of the SV40 gene sequences. Separately, pTM was digested with the same enzymes and the larger the ampicillin resistance gene, again cleaved at the PvuI site, and also the TKneo sequence which provides G418 resistance (see Example 1, section 2). The BamHI site lies beyond the TKneo sequence. On ligation of the two fragments using T4 DNA ligase the amp-r gene is reconstructed and the TKneo sequence and SV40 sequence are assembled in the same plasmid.

The unique HindIII site in pSVTKneo was altered by the addition of an oligonucleotide to provide two further unique restriction sites for enzymes BamHI and XhoI, as described below. Plasmid pKG5 was constructed from the plasmid pSVTKneo. This construction was designed to add unique restriction sites to pSVTKneo in order to increase its general usefulness as an expression vector. Construction details were as follows: (1) pSVTKneo was digested to completion with BamHI and blunt-ended using Klenow fragment of DNA polymerase I. The blunt-ended molecule was self-ligated and the resultant circular molecule transformed into E. coli. The resultant plasmid, designated pKG3, differs from pSVTKneo in that it has acquired four extra base pairs and, as a result has lost the BamHI site of pSVTKneo. (2) pKG3 was digested to completion with HindIII and blunt-ended with the Klenow fragment of DNA polymerase I. The resultant fragment was then ligated to a double stranded synthetic deoxyoligonucleotide:

(5')CTCGAGGATCCA(3')

(3')GAGCTCCTAGGT(5')

encoding the restriction sites for BamHI (GATCC) and XhoI (CTCGAG), and the ligation products were transformed into E. coli. From the transformants, a plasmid designated pKG5 was isolated with the unique restriction sites for HindIII (re-created upon successful ligation) BamHI and XhoI with the orientation of sites as shown in FIG. 3.

3. Insertion of factor IX DNA sequence into plasmid pKG5 to form recombinant plasmid pIJ5/9

1 microgram of p5'G/3'cVI DNA was digested to completion by restriction enzymes BamHI and HindIII and the band containing factor IX sequences electroeluted from an agarose gel. About 100 ng of the eluted material was ligated with 100 ng of plasmid pKG5 that had previously been digested to completion by BamHI and HindIII. The ligation mixture was used to transform E. coli MC1061 and one transformant, pIJ5/9, was shown to have the desired genotype by detailed restriction analysis.

The recombinant plasmid pIJ5/9 in E. coli MC1061 has been deposited as a patent deposit under the Budapest Treaty on the International Recognition of the Deposit of Micro-organisms for the Purposes of Patent Procedure, at the National Collection of Industrial Bacteria, Torry Research Station, PO Box 32, 135 Abbey Road, Aberdeen, Scotland, AB9 8DG, on Jun. 13, 1985 under the number NCIB 12103.

4. Transfection of a mammalian cell line with the recombinant plasmid pIJ5/9 carrying a human factor IX gene pIJ5/9 was introduced into MDCK cells dog kidney cells available from Flow Laboratories Inc., by calcium phosphate—mediated transformation, see Example 1. pIJ5/9 contains the TK/NEO gene and selection was therefore made for G418 resistance. Cells were grown in DMEM, 10% FCS containing penicillin, streptomycin, kanamycin and "Fungizone" as well as 800 micrograms/ml of antibiotic G418 ("Geneticin", GIBCO). Three clones obtained from the transfection of one 9 cm diameter petri dish were subsequently transferred into separate wells (volume of well=2 ml) of a multi-well plate and allowed to grow to confluence. When confluence had been reached, the medium overlaying each clone was removed and analysed for the presence of human factor IX antigen.

5. Confirmation of the secretion of human factor IX

The media from the clones of dog kidney (MDCK) cells transformed with the recombinant DNA plasmid were assayed by sandwich ELISA (see Example 1). Two clones proved negative, whilst media from the third, labelled clone 593, contained human factor IX antigen at a level of more than 10 ng/ml (10 ng/ml was the upper limit assayable in this experiment). Furthermore, a sample of medium from clone 593 was adsorbed for 30 minutes in the presence of barium sulphate (see Example 1). After this incubation, the clarified medium was again assayed for factor IX antigen. 100% of the antigen present was removed by this pretreatment indicating the successful gamma-carboxylation of factor IX by MDCK cells.

In order to test further the factor IX product of clone 593, 50 ml of conditioned growth media were prepared as follows. Five 80 cm$^2$ flasks were each seeded with 593 cells in 10 ml of G418 medium. The flasks were left 4 days until they became confluent and the media were then harvested, pooled, and assayed quantitatively by ELISA for human factor IX antigen. The sample contained 60 ng per ml of factor IX, which is about 1.2% of the concentration found in normal human plasma.

50 ml of this material was purified by passing once through a factor IX monoclonal antibody immunoaffinity column (as described in Example 1) and the bound factor IX antigen was recovered in 1.5 ml of eluant. This preparation was assayed by ELISA and by clotting assay, as described in Example 1. The results of these assays are shown in Table 2, again as % of normal human plasma.

TABLE 2

| Analysis of clotting factor IX activity and human factor IX antigen in purified sample from cell line 593 | |
|---|---|
| Assay Clotting (%) | 15 |
| Clotting, of sample + 3A6 monoclonal antibody (%) | 0 |
| Human factor antigen (%) | 15 |
| Specific activity = $\frac{\text{Clotting activity}}{\text{Antigen concentration}} = \frac{15}{15} = 100\%$ | |

The following conclusions can be drawn from the analyses:

(a) Human factor IX is produced and secreted by cell line (clone) 593.

(b) After growth to confluence, line 593 cells secrete at least 60 ng/ml factor IX antigen into the medium. This is gamma-carboxylated and remains its ability to bind the factor IX monoclonal antibody.

(c) Based on the binding to monoclonal antibody 3A6, 1.125 micrograms of human factor IX was recovered from a total of 3 micrograms applied to an immunoaffinity column (a recovery of 37.5%).

(d) The factor IX is fully active biologically as indicated by levels of antigen and clotting activity in the affinity-purified sample.

The amount of factor IX antigen produced by cell line 593 under normal growth condition was measured as follows. Cells of line 593 were seeded to a density of 50% confluence in a 25 cm$^2$ tissue culture flask. The culture was overlaid with 2 ml of growth medium and incubated at 37° C. in a humidified incubator. At daily intervals the conditioned medium was removed and replaced with fresh.

Figure 4:
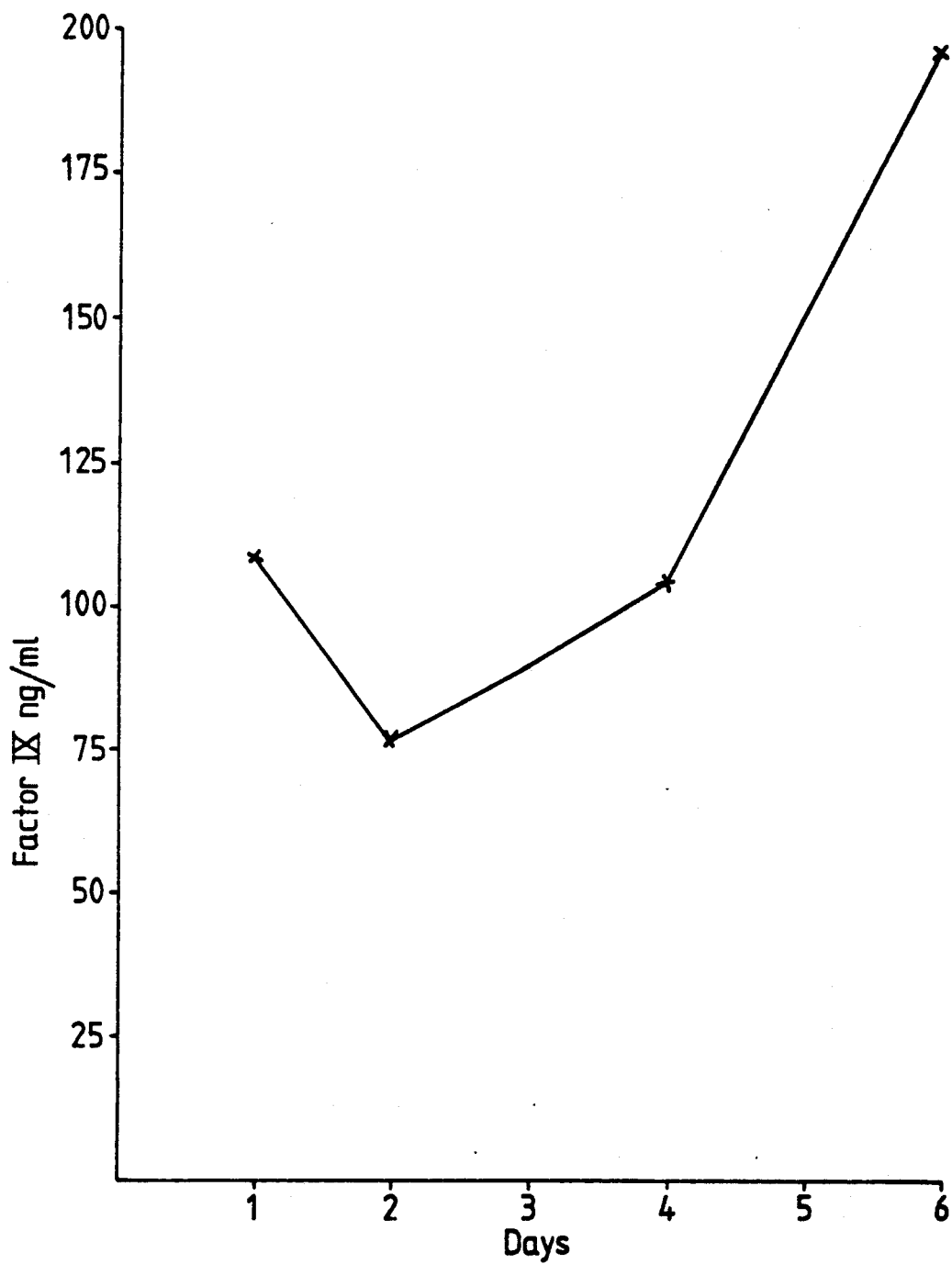
FIG. 4 is a graph showing factor IX levels expressed from a monolayer of confluent mammalian cells transfected with the expression vector of FIG. 3.

Factor IX antigen was assayed in each sample by a quantitative ELISA assay and the results plotted as shown in FIG. 4. It will be seen that the cells at 50% confluence or greater, secrete in the order of 100 ng/ml factor IX antigen per day (a level equal to about 2% of that found in normal serum).

The unusually high value on day 1 could be due to carry-over in the inoculum sample and the 200 ng/ml value found on day 6 represents the accumulated factor IX of 2 days secretion.

EXAMPLE 3

In this example, another dog kidney cell clone, clone C6, was isolated, which gave an improved yield of factor IX protein of the invention to that of clone 593 reported in Example 2 above. This improved cell line was grown in Spinner culture over a period of 3 weeks in the absence of antibiotic G418 to establish its utility for producing factor IX protein in large amounts and in a continuous process without the requirement for antibiotic G418, at considerable saving in expense.

Factor IX protein from clone C6, purified by a slightly different immunoaffinity method to that described in Example 2, again gave material which was more than 90% biologically active and was shown to have greater than 90% of the rDNA factor IX protein of the invention as the correct molecular weight product essentially identical to authentic blood-derived factor IX.

1. Transfection of the dog kidney cell line with the recombinant pIJ5/9 carrying a human factor IX gene This was carried out exactly as described in Example 2, section 4 above, except that 90 G418 resistant clones were obtained from the transfection of ten 9 cm diameter petri dishes. These clones were subsequently transferred onto separate wells of a multi-well plate and allowed to grow to confluence. The medium in which the cells were growing was then removed for the analysis of human factor IX antigen by ELISA as described in Example 1, section 5 above. Thirty clones were found to be positive, as judged by having greater than 10 ng/ml factor IX. These 30 clones were then seeded into a further multi-well plate and grown again to confluence. The medium was again assayed for factor IX antigen by ELISA, after diluting each sample by a factor of 10. Five clones had greater than 100 ng/ml of factor IX. These clones were then seeded into flasks of effective surface area 25 cm$^2$ and again grown to confluence, followed by assay of the medium by ELISA for factor IX antigen. One clone, designated C6, produced 250 ng/ml of factor IX antigen in this experiment, and was judged to be the highest producing cell line.

2. Characterisation of cell line C6

To confirm that the factor IX gene had been introduced permanently into the chromosome of the dog kidney cells, the following test was carried out. DNA was isolated from the nuclei of cells derived from growth in a flask of effective surface area 75 cm$^2$ of confluent C6 cells by established procedures (Maniatis et al., Molecular Cloning: A Laboratory Manual, Cold Spring Harbor, N.Y., 1982). Isolated DNA was subject to double digestion with the restriction endonucleases HindIII and BamHI which produce a 1.6 Kb restriction fragment from the integrated pIJ5/9 plasmid of human factor IX (see FIG. 3). This was analysed by Southern blotting using $^{32}$P nick translated human factor IX cVI, Anson et al., EMBO J. 3, 1053–1060, (1984), as a probe. A band having the correct mobility was detected on the Southern blot and its intensity relative to a marker track of a corresponding analysis of the same amount of DNA from the cell line 4A (see Example 1, section 4 above) suggested that there were between 3 and 5 copies of the gene present.

3. Characterisation of the human factor IX produced

Initially a 10 ml volume of conditioned medium derived from the growth of C6 cells was analysed for the ability of the factor IX to adsorb to barium sulphate (see Example 1 above). In one experiment more than 98% of the material became bound, suggesting the factor IX was essentially completely gamma-carboxylated.

In further small scale experiments designed to test whether factor IX of the correct molecular weight was synthesised, we assayed by polyacrylamide gel electrophoresis the factor IX protein which was adsorbed by barium sulphate from another 10 ml of conditioned medium. This material was fractionated on a 10% Laemmli polyacrylamide gel. After Western blotting, human factor IX antigen was detected by ELISA using a polyvalent rabbit anti-human factor IX antibody (Calbiochem) followed by development with an alkaline phosphatase linked goat anti-rabbit IgG antibody (Sigma). After the ELISA a stained band was observed with a mobility indistinguishable from authentic factor IX isolated from normal pooled human plasma by the same procedure. No slower or faster bands were detected and the stined band which corresponded to authentic factor IX was absent in a control sample prepared from conditioned media derived from control (non-factor IX producing) MDCK cells.

In a further experiment to test for the authenticity of the factor IX protein of the invention produced from cell line C6, 0.5 ml medium from the growth of C6 as above was immunoprecipitated by adsorption onto beads of "Sepharose 4B" to which a mouse anti-factor IX antibody was covalently attached using cyanogen bromide. Factor IX bound to the beads was eluted by boiling with 1% SDS and 3% 2-mercaptoethanol and the solution applied to the origin of a 10% polyacrylamide gel as above. Western blotting was carried out using a mouse monoclonal anti-factor IX antibody A7 (see section 5), $^{125}$I labelled or by ELISA using a polyclonal anti-factor IX antibody. Any antibody which reacts with the denatured factor IX obtained by SDS-PAGE can be used.

Two Western blots from the factor IX protein of the invention produced by cell line C6 were compared separately with Western blots from (a) normal human plasma and (b) the plasma of a patient suffering from a rare variation of typical Christmas disease. To explain briefly control (b), the patient, coded "Ox 3", suffered from a blood-clotting deficiency of the Christmas disease type, despite having a normal level (89%) of factor IX-like antigen as measured immunologically. Ox 3's factor IX-like antigen is a protein of slightly higher molecular weight that normal factor IX. Recombinant DNA research on Ox 3 showed that his gene suffered from a point mutation at the arginine (R) codon at the amino acid position −4, see FIG. 2 of the Anson et al. 1984 paper. As a result the precursor molecule, which is produced as the primary translation product in the liver, could not undergo all the cleavage operations necessary to give factor IX. The genetic disorder therefore gives rise to a factor IX-like protein having 18 additional amino acids of the prepeptide and propeptide sequence, beyond the N-terminal end of factor IX proper. Full details of the research are given in a paper by A. K. Bentley, D. J. G. Rees, C. Rizza and G. G. Brownlee, Cell in press.

The gels for the control Western blots were obtained as follows. The plasma from the normal patient and from patient Ox 3 was concentrated 6-fold by adsorption and elution from barium citrate. 10 microlitre aliquots were boiled in 1% SDS/2.5% 2-mercaptoethanol and applied to the origin of an 8% Laemmli polyacrylamide gel.

The results showed clearly that the factor IX secreted by the cell line C6 has a molecular weight indistinguishable from the control factor IX of normal plasma, but about 2,000 daltons less than that of the factor IX-like protein of Ox 3. Such a molecular weight difference is wholly accounted for by the additional 18 amino acids (of average molecular weight, say, 112) in the factor IX-like protein of Ox 3. No evidence of a significant amount (greater than 2%) of aberrant forms of higher or lower molecular weight protein related to factor IX could be seen in the Western blots of the factor IX protein of the invention.

4. Growth of larger volumes of clone C6 in Spinner culture and purification of factor IX Clone C6 cells were seeded at approximately 10 cells per bead onto 2 g of microcarrier beads, (Gibco 60-085-12; note; Cytodex 3 microcarriers, Pharmacia, have also been used in other experiments) in a volume of 400 ml of DMEM, 10% FCS containing penicillin, streptomycin, kanamycin and "Fungizone" in a commercial Spinner vessel (Techne). No antibiotic G418 was added to the medium, preliminary experiments having shown that there was no difference in the yield of factor IX obtained from the clone 593 described in Example 2 above when it was cultured over a period of 14 days (including 2 sub-culturing steps), whether or not the antibiotic was present in the medium.

Samples were removed from the Spinner culture and assayed for factor IX antigen by the ELISA method (see above). The concentration of factor IX in the medium rose to a plateau at 6–8 days of 375 ng/ml. Replacing the spent medium with fresh medium allowed the cells attached to the microcarriers to synthesise more factor IX, which then reached a concentration of 280 ng/ml in the medium on day 12. A further medium change on the day 12 allowed cells to continue to produce more factor IX, reaching 150 ng/ml on day 17.

It was concluded that clone C6 can produce factor IX over a period of 2–3 weeks from a microcarrier suspension without the need for and expense of the addition of antibiotic G418. This experiment and repetitions thereof show that yields of factor IX are 150 to 200% higher in Spinner culture than in stationary culture flasks, presumably because of the higher density of cells present per unit volume of medium.

5. Purification and activity of factor IX derived from cell line C6 in Spinner culture Two litres of conditioned media from two experiments similar to that of section 4 above were pooled and the factor IX protein concentrated by adsorption on barium sulphate. After elution, the protein was subjected to immunoaffinity chromatography using the mouse monoclonal antibody A7 specific for a metal ion dependent epitope on the light chain (N-terminal region) of factor IX (a gift from Dr. K. Smith, University of New Mexico, Albuquerque, USA), who also provided the chromatographic protocol. The affinity column was prepared by activation of Affigel 10 (BioRad) resin using the monoclonal antibody as recommended by the manufacturer which gave a column material with 8 mg antibody bound per ml or packed resin (and with a capacity of purification of approximately 4 mg of factor IX per ml of resin). The factor IX sample was loaded (at 4° C.) n "initial buffer" comprising 0.5M NaCl, 0.02 M Tris/HCl, pH 7.2, 0.02M $MgCl_2$, 0.001M phenylmethylsulphonyl fluoride (PMSF), and the column washed with 100 column volumes of "initial buffer". The column was then washed with 50 volumes "high salt buffer" in which 1M NaCl replaced the 0.15M NaCl of the "initial buffer", factor IX was eluted using the "elution buffer" which differed only from "initial buffer" in that 0.02M $MgCl_2$ was replaced with 0.02M EDTA and the PMSF was omitted. Human factor IX was assayed in the subsequent 20 ml fractions by ELISA and the factor IX containing fractions were pooled and dialysed against 0.15M NaCl, 0.02M Tris/HCl pH 7.2. 4 ml of dialysate was obtained which contained 12.0 micrograms/ml of human factor IX antigen as assayed by quantitative ELISA. Table 3 below shows the results of the ELISA for antigen and for a one stage clotting assay as described in Example 1. Percentages are those of normal human plasma.

TABLE 3

| Analysis of clotting activity and human factor IX antigen in purified sample from Spinner cultured cell line C6 | |
|---|---|
| Assay | Cell line C6 |
| Clotting (%) | 240 |
| Human factor IX antigen (%) | 264 |
| Specific activity = $\frac{\text{Clotting activity}}{\text{Antigen concentration}} = \frac{240}{264} = 91\%$ | |

It was concluded from these results that the C6 cells secrete near-fully biologically active factor IX protein.

We claim:

1. A plasma-free preparation suitable for use in the treatment of human patients suffering from deficiency of factor IX, said preparation comprising as active ingredient biologically active recombinant DNA-derived factor IX protein derived from a single human individual and which (1) essentially has the amino acid sequence of human factor IX protein, (2) is free from contamination by poxviruses and by all human plasma constituents, and (3) has a specific activity defined as the concentration of test sample required to clot a given volume of factor IX-deficient plasma in a given time by the kaolin-cephalin method divided by the concentration of the factor IX protein in the test sample as determined by ELISA, of at least 90% of that of average normal human plasma.

2. A preparation according to claim 1, wherein said factor IX protein has a specific activity of 100%

3. A method of treating a human patient suffering from a deficiency of factor IX, said method comprising the step of administering to said patient a plasma-free preparation comprising as active ingredient a biologically active recombinant DNA-derived factor IX protein derived from a single human individual which (1) essentially has the amino acid sequence of human factor IX protein derived from a single human individual which (1) essentially has the amino acid sequence of human factor IX protein, (2) is free from contamination by poxviruses and by all human plasma constituents, and (3) has a specific activity defined as the concentration of test sample required to clot a given volume of factor IX-deficient plasma in a given time by the kaolin-cephalin method divided by the concentration of factor IX protein in the test sample as determined by ELISA, of at least 90% of that of average normal human plasma.

4. A method according to claim 3, wherein said factor IX protein has a specific activity of 100%.

* * * * *